United States Patent [19]
Bellis

[11] Patent Number: 5,110,954
[45] Date of Patent: May 5, 1992

[54] DEHYDROGENATION OF DIOLS

[75] Inventor: Harold E. Bellis, Wilmington, Del.

[73] Assignee: E. I. Du Pont de Nemours and Company, Wilmington, Del.

[21] Appl. No.: 551,124

[22] Filed: Jul. 11, 1990

[51] Int. Cl.⁵ .............. C07D 313/04; C07D 309/10; C07D 307/20

[52] U.S. Cl. .................. 549/266; 549/274; 549/295; 549/328

[58] Field of Search ............ 549/266, 273, 295, 328

[56] References Cited

U.S. PATENT DOCUMENTS

| | | | |
|---|---|---|---|
| 3,817,996 | 6/1974 | Snapp, Jr. | 260/244 R |
| 4,433,175 | 2/1984 | Kaufhold | 568/471 |
| 4,465,847 | 8/1984 | Shvo | 549/295 |
| 4,486,607 | 12/1984 | Webb | 568/425 |
| 4,960,906 | 10/1990 | Drent | 549/273 |

FOREIGN PATENT DOCUMENTS

| | | | |
|---|---|---|---|
| 0123482 | 7/1985 | Japan | 549/273 |
| 1246173 | 11/1986 | Japan | 549/328 |
| 193487 | 3/1967 | U.S.S.R. | |

OTHER PUBLICATIONS

Berthon et al., Preparation D'Esters Par Deshydrogenation D'Alcools . . . , Tetrahedon Letters, vol. 22, No. 41, pp. 4073-4076, 1981.

Nanavati, "Catalytic Dehydrogenation of Alcohols," J. Indian Chem. Soc., vol. LI, May 1974, pp. 551-552.

Reeve et al., "Catalytic Dehydrogenation of Alcohols in the Liquid Phase Using Ethylene as a Hydrogen Acceptor," Oct. 1940, 2874-76.

Primary Examiner—C. Warren Ivy
Assistant Examiner—Amelia A. Owens
Attorney, Agent, or Firm—Charles E. Krukiel

[57] ABSTRACT

A process is provided for the production of lactones by the catalytic dehydrogenation of aliphatic diols containing from 3-7 carbon atoms and optionally one or more ether linkages in the diol chain. The reaction is conducted in the liquid phase with a copper chromite catalyst at a temperature of from about 150°-250° C. in the absence of added hydrogen, and preferably at reaction conditions where yields are about 99%.

10 Claims, No Drawings

DEHYDROGENATION OF DIOLS

BACKGROUND OF THE INVENTION

The present invention relates in general to a process for the production of high purity lactones in high yield which is conducted in the liquid phase using a class of copper chromite catalysts, preferably, in the form of a slurry.

It is known to catalytically dehydrogenate monohydric alcohols to produce aldehydes or ketones. Further in the case of aliphatic diols, B. Berthon et al., Tetrahedron Letters 22 (41) 4073-6 (1961), describes the liquid phase copper oxide catalyzed dehydrogenation of four to six carbon atom diols to produce the corresponding lactones. This article also describes the production of gamma butyrolactone from butanediol.

The use of a copper chromite catalyst to convert butanediol to gamma butyrolactone is disclosed in U.S.S.R. Patent No. 193,487. This reaction is conducted in the vapor phase in the presence of hydrogen.

The dehydrogenation of aliphatic diols to form unsaturated cyclic ethers, such as 2,3-dihydrofuran from butanediol rather than such lactones, is disclosed in U.S. Pat. No. 3,817,996. This process is conducted in the liquid phase and the product is recovered in the liquid phase using a copper chromite/tungstic oxide catalyst in the presence of hydrogen.

U.S. Pat. No. 4,433,175 discloses that a catalyst comprising 35% CuO, 38% CrO$_3$, 10% BaO, and, optionally, a silica binder can be used for the dehydrogenation of neohexanol to yield neohexanal. It should be noted that the chromium in this catalyst is hexavalent, whereas in the catalyst used in the present invention it is trivalent. The reaction is conducted in the vapor phase, and the product is recovered by separate distillation. High yield and product purity were obtained at low conversion of neohexanol.

U.S. Pat. No. 4,486,607 discloses the dehydrogenation of 3-(t-butylphenyl)-2-methylpropan-1-ol in the presence of a copper chromite catalyst suspension to yield the corresponding aldehyde. Product recovery is by distillation from the reactor.

W. Reeve et al., JACS 62,2874 (1940), discloses dehydrogenating alcohols having four or more carbon atoms per molecule to give aldehydes or ketones using a barium-activated copper chromite catalyst in the liquid phase, using ethylene as a hydrogen acceptor. Yields and conversions are low.

The preparation of ketones by the dehydrogenation of secondary alcohols in the liquid phase using a copper chromite catalyst is described by D. D. Nanvati, J. Ind. Chem. Soc 51 (5), 551-2 (1974). The products are recovered by filtration and subsequent purification by distillation. An almost quantitative yield of 2-octanone was obtained from 2-octanol.

There remains a need to provide a process for dehydrogenating aliphatic diols at high conversion to produce lactones of high purity in excellent yield. It is also desirable to provide a catalyst for such a process which will retain its catalytic activity over a long duration.

SUMMARY OF THE INVENTION

According to the present invention, high purity lactones are produced by the catalytic dehydrogenation and cyclization of aliphatic diols by heating a slurry (preferably) of a copper chromite catalyst and an aliphatic diol to form the corresponding lactone, preferably in the substantial absence of added hydrogen. The diol may be diluted by the addition of inert solvents or even product but at some loss of productivity, e.g., by the recycling of an impure product stream. In preferred aspects, the reaction can be carried out to form lactones using aliphatic diols containing from 3-7 carbon atoms in the chain; a slurry of copper chromite catalyst and the aliphatic diols is heated to a temperature of from about 150° to 250° C. in the absence of hydrogen; and the reaction is conducted with butanediol to produce high yields of γ-butyrolactone.

According to the present invention, it was unexpectedly discovered that when a preferred slurry of a particulate copper chromite catalyst in a diol having 3-7 atom chains and optionally alkyl substituents is heated, in the absence of added hydrogen, the diol is dehydrogenated to the corresponding lactone in high yields surpassing those of the vapor phase reaction, while the catalyst retains its activity for periods far in excess of those obtained for gas phase reactions, even in the presence of hydrogen. The product is preferably recovered by distillation or, alternatively, the catalyst can be separated from the product by filtration and subsequently purified if need be by distillation or other techniques known to the art. Further, surprisingly, the process of the present invention results in unexpectedly high yields of high purity lactones.

A preferred process of the present invention can be illustrated by the following Equation I:

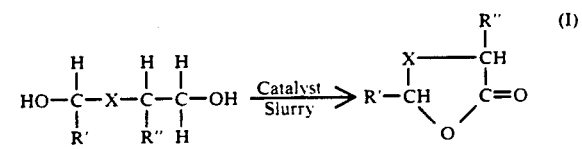

where:

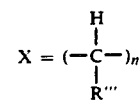

n = 0 to 4

R', R" and R"" = H or alkyl containing 1-4 C atoms.

In another aspect of the present invention, the diol chain may contain one or more ether linkages, i.e., the chain may contain one of more non-adjacent oxa atoms, for example, diethylene glycol which, by the process of this invention, would give p-dioxanone; preferably, the number of atoms in the diol main chain, including non-adjacent oxa atoms, is still 3-7.

In a preferred aspect of the present invention, butanediol is converted to gamma butyrolactone according to the reaction shown in Equation II:

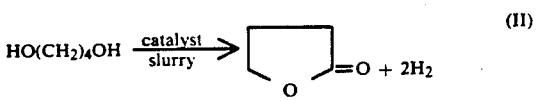

Illustrative aliphatic diols described in Equation I above include, among many others, diethylene glycol; 1,3-propanediol; b 1,4-butanediol; 1,5-pentanediol; 1,6-hexanediol; 6-propyl-4,7-heptanediol; 2,4-diethylpentanediol; 5,7-heptanediol; 4,6-dimethyl-2,7-heptanediol.

The process of the present invention can be used to prepare lactones having 4 to 8 atom rings. Preferred lactones produced by this process are b-propyrolactone, g-butyrolactone, g-valerolactone, d-valerolactone, and p-dioxanone.

Copper chromite catalyst compositions, $(CuO)_x(Cr_2O_3)_y$, useful in the process of the present invention are generally available commercially in particulate form. The proportion of copper expressed as CuO and chromium expressed as $Cr_2O_3$ can vary from about 40–75 wt. % CuO and 25–60 wt. % $Cr_2O_3$. Catalyst compositions containing from about 40–55 wt. % CuO and 40–50 wt. % $Cr_2O_3$ are preferred. Examples of such commercially available catalysts are United Catalyst, Inc. G-13 powder, which nominally contains 53 wt. % CuO and 38 wt. % $Cr_2O_3$, and Harshaw 1800 powder, which possesses 51 wt. % CuO and 47 wt. % $Cr_2O_3$.

It has been found that from the standpoint of catalyst stability, i.e., effective catalyst life, $(CuO)_x(Cr_2O_3)_y$ compositions also containing the oxides of barium or manganese or their combinations are preferred, although other heavy metal oxides may also be advantageous.

In the preferred catalyst compositions, the barium oxide can amount to 3–15 wt. % and the manganese oxide to 2–5 wt. %. Examples of such catalysts are United Catalyst, Inc. G-22, which nominally contains 41 wt. % CuO, 40 wt. % $Cr_2O_3$, and 11 wt. % BaO; United Catalyst, Inc. G-89, which contains 49 wt. % CuO, 45 wt. % $Cr_2O_3$, and 3 wt. % MnO; and United Catalyst, Inc. G-99, which contains 44 wt. % CuO, 45 wt. % $Cr_2O_3$, 4 wt. % BaO, and 2 wt. % MnO.

Any of the copper chromite based catalysts can be supported on any silica high surface area, attrition-resistant material, e.g., as discussed further below.

Preferably, the catalyst particles are in the size range of from about 1–20 microns, more preferably about 5 microns. This is a suitable particle size range for the incorporation of a reactive catalyst suspension, and yet the catalyst can be retained on a fritted glass filter having a pore size of about 2 microns. In commercial scale production, a metal cartridge filter or a cloth filter capable of retaining particles larger than 1 micron can be used.

One of the unexpected advantages of the process of the present invention is the long catalyst life, especially in view of the prior art prejudices described above. For example, when a catalyst comprising 49 wt. % CuO, 45 wt. % $Cr_2O_3$ and 3 wt. % MnO was used in the dehydrogenation of butanediol according to the present invention, it was surprisingly found to retain its catalytic activity in excess of 1000 hours. Other advantages of the process of this invention over vapor phase dehydrogenation include ease of catalyst replacement, lowered energy consumption, and lowered capital investment.

If the product is to be separated from the catalyst by filtration, any reduction in the size of the catalyst particles caused by mechanical abrasion is undesirable. When the catalyst particles become too small, they can pass through the filter. Consequently, catalyst can be lost and the product contaminated with catalyst fines. It is, therefore, preferred to use an agglomerated catalyst in these instances, which is more resistant to abrasive disintegration.

An agglomerated catalyst can be prepared by precipitating copper ammonium chromate onto an inert high surface area substrate, such as kieselguhr, alumina, silica, or a zeolite which is strong enough to withstand the disruptive effect of slurrying in the process of the present invention. The substrate can be mixed with solutions containing the desired proportions of copper nitrate and ammonium chromate. The solids recovered by filtration are washed to remove ammonium nitrate and heated to yield strong aggregates coated with copper chromite. These aggregates can be used effectively in a slurry for several thousand hours without any significant deterioration.

The attrition resistance of a copper chromite catalyst powder can also be increased by slurrying it with a colloidal silica sol, such as Du Pont Ludox AS 40, and spray drying to obtain a powder. Such powders are useful in the process of the present invention because when used in a slurry, they retain their integrity over more extended periods.

One version of the process of the present invention for producing lactones can be carried out by charging the diol and catalyst to a reactor optionally provided with a heating means, an agitator and a condenser. The diol and catalyst are stirred to form a slurry and the temperature is raised to produce mild reflux conditions. The reaction can be monitored by periodically taking samples and analyzing them by gas chromatography to determine the extent of conversion of the diol to the desired product, and whether by-products have formed in any significant amounts. The dehydrogenation process is usually 90–100% complete in two to four hours. The product can be separated either by distillation or by using a microfilter of the type previously described.

In another embodiment, the reaction is conducted in the liquid phase by passing the liquid reactants through a fixed bed of the catalyst. The liquid reactants can be sprayed into such a fixed bed, or a trickle bed reactor can be used.

The process of the present invention can be carried out continuously by establishing steady state conditions and maintaining a constant volume in the reactor by continuously adding fresh diol in stoichiometric equivalence to the recovered product. This procedure can be used when the product is recovered either by distillation or filtration.

The hydrogen liberated during the reaction can be vented from the reactor and disposed of in a safe manner, such as by burning, after passing through a flash arrestor.

Any higher boiling byproducts formed in the reaction, such as tetrahydrofuran butanediol acetal (TBA), accumulate in the reactor when the product is removed from the reactor by distillation. These byproducts are known to have an adverse influence on the life of the catalyst. However, the extent to which such byproducts are formed depends upon the catalyst. With the preferred catalysts of this invention, these byproducts equilibrate at a very low level, less than about 1%; and, in this case, a catalyst life of more than 2000 hours has been demonstrated. When filtration is used to recover the product, any impurities formed are also removed from the reactor with the product; consequently, the possibility of any adverse effect on catalyst life is minimal, and all copper chromite catalysts exhibit adequate life. Product purity is generally 98% or better, which can be improved even further by subsequent distillation.

Preferably, the amount of copper chromite catalyst is from about 1–20 wt. %, more preferably from about 5–10 wt. %, based on the diol charged to the reactor.

It is preferred that the reaction be conducted at a temperature in the range of from about 150°–250° C. in order to take full advantage of the catalyst activity. If the boiling point of the starting diol is too low, e.g., less than 150° C., it will be necessary to pressurize the reactor in order to reach an efficient operating temperature. In the case of high boiling lactones, vacuum may be applied to facilitate removal of the product by distillation.

Using routine optimization of reaction conditions in light of the guidance provided above, nearly quantitative yields, based on diol consumed, are readily achievable.

The lactones produced by the process of this invention are all useful as solvents and intermediates in organic synthesis. For example, butyrolactone is used to prepare pyrrolidone by reaction with ammonia, and N-methyl pyrrolidone by reaction with methylamine and vinyl pyrrolidone by reaction with ammonia followed by acetylene.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth in degrees Celsius; and, unless otherwise indicated, all parts and percentages are by weight.

The entire texts of all applications, patents and publications, cited above and below are hereby incorporated by reference.

EXAMPLES

Example 1

This example shows the conversion of butanediol (BDO) to gamma butyrolactone (GBL) using a 5% loading of a copper chromite catalyst. A 250 ml round bottom flask fitted with a stirrer and a Vigaraux condenser was charged with 150 g butanediol and 7.5 g copper chromite catalyst G-13 from United Catalyst, Inc. The reactor was heated to 195.C; samples were periodically taken, centrifuged to remove catalyst, and then analyzed by gas chromatography. The compounds analyzed by gas chromatography were butanediol (BDO), gamma butyrolactone (GBL), gamma hydroxybutyraldehyde (GHBA), and tetrahydrofuran butanediol acetal (TBA). The results obtained for samples taken at the times indicated are listed in Table 1.

TABLE 1

| Time min. | Temp. °C. | BDO wt. % | GBL wt. % | GHBA wt. % | TBA wt. % | Others wt. % |
|---|---|---|---|---|---|---|
| 30 | 194 | 54.88 | 42.88 | 0.29 | 1.88 | 0.07 |
| 60 | 194 | 30.23 | 67.40 | 0.21 | 2.12 | 0.04 |
| 90 | 193 | 12.51 | 85.25 | 0.09 | 2.13 | 0.02 |
| 120 | 194 | 03.79 | 94.36 | 0.04 | 1.80 | 0.01 |
| 150 | 196 | 00.94 | 98.08 | 0.00 | 0.94 | 0.04 |
| 180 | 195 | 00.45 | 97.91 | 0.00 | 1.63 | 0.01 |
| 220 | 195 | 00.49 | 97.92 | 0.00 | 1.59 | 0.00 |

At the conclusion of the reaction, the product was recovered by distillation at atmospheric pressure. Gamma butyrolactone of 99.16% purity was recovered, b.p. 205° C., and 156.1 g of the original charge of 157.5 g were accounted for. Analysis of the data shows a first order rate dependency on the BDO concentration, with a half-life of 22 minutes. The higher boiling species, TBA, and unreacted BDO remained with the catalyst in the reactor.

Example 2

This example shows the conversion of BDO to GBL using a 5% loading of a barium/copper chromite catalyst. The procedure of Example 1 was repeated using a barium-promoted copper chromite catalyst, G-22 from United Catalyst, Inc., at the same 5% loading based on the butanediol charge.

Analysis by gas chromatography of samples taken at the times indicated are listed in Table 2.

TABLE 2

| Time min. | Temp. °C. | BDO wt. % | GBL wt. % | GHBA wt. % | TBA wt. % | Others wt. % |
|---|---|---|---|---|---|---|
| 35 | 193 | 73.13 | 24.96 | 0.35 | 1.50 | 0.06 |
| 90 | 195 | 47.32 | 50.52 | 0.36 | 1.78 | 0.05 |
| 180 | 195 | 15.86 | 82.12 | 0.13 | 1.87 | 0.03 |
| 210 | 193 | 10.98 | 87.05 | 0.10 | 1.87 | — |

The GBL product was recovered by distillation at 205° C. The GBL purity was 97.6% and 154.8 g of the original charge of 157.5 g was accounted for. Analysis of the data shows a first order rate dependency on BDO concentration and a half-life of 65 minutes. cl Example 3

This example is similar to Example 2, except that a manganese/copper chromite catalyst, G-89 from United Catalyst, inc., was used at a 5% loading.

Analysis by gas chromatography of samples taken at the times indicated are listed in Table 3.

TABLE 3

| Time min. | Temp. °C. | BDO wt. % | GBL wt. % | GHBA wt. % | TBA wt. % | Others wt. % |
|---|---|---|---|---|---|---|
| 30 | 193 | 71.26 | 25.58 | 0.35 | 2.58 | 0.23 |
| 60 | 192 | 58.29 | 38.04 | 0.33 | 3.27 | 0.07 |
| 120 | 193 | 20.43 | 75.31 | 0.15 | 4.08 | 0.03 |

The GBL product was recovered by distillation as described in Example 1. Analysis of the data shows a first order rate dependency on BDO concentration and a half-life of 65 minutes.

EXAMPLE 4

This example is similar to Example 1, with the modification that product is continuously removed overhead. A 2 l round bottom flask was fitted with a stirrer and a seven-plate condenser. The flask was charged with a slurry of BDO, and the catalyst was increased to 10 wt. % of a copper chromite catalyst powder, G-13 from United Catalyst, Inc. The initial charge of 1000 g BDO and 100 g of catalyst was heated to 205° C., with continuous stirring to maintain a slurry. After 45 minutes, the GBL product was taken off overhead, and BDO was fed continuously at a rate sufficient to keep a constant level in the reaction flask. The BDO feed rate and the heat input were adjusted to maintain a steady state. At a feed rate of 2.5 g/min, GBL product was recovered at 2.4 g/min over a period of 48 hours. The purity of the GBL averaged 99.2%. Other components were GHBA (0.3%), BDO (0.4%), and a trace of tetrahydrofuran. This reaction was discontinued after 100 hours because the catalyst was no longer effective.

EXAMPLE 5

The procedure of Example 4 was repeated using a manganese/copper chromite catalyst, United Catalyst, Inc. G-89. Product was taken off overhead for 1000 hours, with no significant reduction of catalyst activity. The purity of the GBL obtained was 99.5%.

EXAMPLE 6

This example is similar to Example 1, except that the product is separated from the catalyst by filtration. The procedure and charge were the same as described in Example 1, with the difference that the unit was kept under total reflux at 195° C. and atmospheric pressure for 6 hours. Product was then continuously removed from the reactor through a fine (0.5 micron) internal filter that separated catalyst from product. BDO was fed to the reactor at a rate corresponding to a hold-up time of 2 hours, maintaining steady state conditions in the reactor. The product analyzed as 95.1% GBL and 3.2% BDO. The filtration recovery process ran smoothly over a period of 6 hours, until the filter plugged due to the accumulation of catalyst fines resulting from abrasion of the catalyst.

EXAMPLE 7

In this example, a spray-dried silica-treated catalyst is prepared and used in the dehydration of BDO to produce GBL. The product is separated from the catalyst by filtration.

Preparation of catalyst

Fifty grams of manganese promoted/copper chromite (United Catalyst Inc., G89), 125 grams of a colloidal silica sol (Du Pont Ludox AS40) and 125 ml of deionized water were mixed by stirring in a 500 ml beaker for 5 minutes. The resulting slurry was a black viscous suspension which was diluted by the addition of a further 125 ml of deionized water to facilitate pumping the slurry through the spray dryer nozzle.

The slurry was spray dried using a Buchi 190 Minispray dryer with a 0.7 mm nozzle. The spray dryer conditions were:

| | |
|---|---|
| Inlet temperature | 228° C. |
| Outlet temperature | 101° C. |
| Pump setting | 6.0 |
| Flow reading | 650 |
| Aspirator reading | 20.0 |

Electron microscopy showed the resulting powder to consist mostly of doughnut- and amphora-shaped particles.

The particle size distribution of the silica-treated catalyst, determined using a Microtrac Particle Size Analyzer, was considerably narrower than that of the original catalyst powder. The average particle size was 10.5 microns versus 7.5 microns for the starting powder. Analysis of the EDAX procedure showed that the spray-dried powder contained silicon, copper, chromium, and manganese.

When the spray-dried, silica-treated catalyst powder and the original untreated catalyst powder were subjected to identical sonic attrition testing, the former was found to be considerably more abrasion resistant. After 10 minutes sonification, the average particle sizes were 5.8 microns and 2.3 microns, respectively.

The procedure of Example 1 was carried out using 5 wt. % of the spray-dried, silica-treated catalyst, based on the BDO, instead of the copper chromite catalyst. The slurry of BDO and silica-supported catalyst was kept under total reflux at 195° C. and atmospheric pressure for 6 hours. Product was then continuously removed from the reactor through a fine (0.5 micron) internal filter. BDO was fed to the reactor at a rate corresponding to a hold time of 2 hours, maintaining steady state conditions in the reactor. The product analyzed as 99.0% GBL. Further purification was accomplished by distillation.

The filtration recovery process ran smoothly over a period of 16 hours and was then discontinued without any significant accumulation of catalyst fines, due to the excellent abrasion resistance of the silica-treated catalyst.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for producing high purity lactone comprising catalytically dehydrogenating an aliphatic diol, wherein the aliphatic diol contains from 3-7 carbon atoms in the main chain and is optionally substituted by $C_{1-4}$ alkyl, in a liquid slurry in the presence of a copper chromite catalyst wherein the catalyst is present in the slurry in particulate form having a size range of from 1-20 microns and in the substantial absence of added hydrogen.

2. The process of claim 1, wherein the aliphatic diol contains one or two etheric-oxygen atoms in its main chain.

3. The process of claim 1, wherein the catalyst is supported on an inert high surface area substrate comprising silica.

4. The process of claim 11, wherein the inert high surface area substrate is kieselguhr, alumina, or a zeolite.

5. The process of claim 1, wherein the amount of catalyst in the slurry is about 1-20 wt. % based on the amount of diol.

6. A process for the production of a lactone having from 4-8 carbon atoms in the ring comprising catalytically dehydrogenating an aliphatic diol having a main chain containing from 3-7 carbon and one or two etheric oxygen atoms, in the presence of a copper chromite catalyst slurried in the aliphatic diol, at a temperature of about 150°-250° C. in the absence of added hydrogen.

7. The process of claim 6, wherein the catalyst contains from about 5 to 15 wt. % of barium oxide or from about 2 to 5 wt. % of manganese oxide.

8. In a process for the production of butyrolactone by the catalytic dehydrogenation of butanediol, the improvement comprising heating a slurry of a copper chromite catalyst in butanediol to a temperature of from about 150°-250° C. in the absence of added hydrogen.

9. The process of claim 8, wherein the catalyst contains about 40-55 wt. % of copper oxide and about 40-50 wt. % of chromium oxide, the catalyst is present in particulate form having a size range of from about 1-20 microns, the catalyst is supported on an inert high surface area substrate, and the amount of catalyst in the reaction mass is from about 5-10 wt. % based on the diol.

10. The process of claim 8, wherein the catalyst comprises a powder obtained by spray drying a slurry of a copper chromite catalyst in a colloidal silica sol.

* * * * *

UNITED STATES PATENT AND TRADEMARK OFFICE
CERTIFICATE OF CORRECTION

PATENT NO. : 5,110,954
DATED : May 5, 1992
INVENTOR(S) : Harold Edward Bellis and Jo-Ann T. Schwartz It is certified that error appears in the above-identified patent and that said Letters Patent is hereby corrected as shown below:

On the Title page, under item [19] "Bellis" should be --Bellis et al. --; and in item [75], Inventors should read:

Harold Edward Bellis and Jo-Ann Theresa Schwartz

Signed and Sealed this

Twenty-fifth Day of January, 1994

Attest:

BRUCE LEHMAN

Attesting Officer     Commissioner of Patents and Trademarks